(12) United States Patent
Caccuri et al.

(10) Patent No.: US 8,796,317 B2
(45) Date of Patent: Aug. 5, 2014

(54) USE OF 7-NITRO-2,1,3-BENZOXADIAZOLE DERIVATIVES FOR ANTICANCER THERAPY

(75) Inventors: Anna Maria Caccuri, Rome (IT); Giorgio Ricci, Rome (IT)

(73) Assignee: Universita Degli Studi di Roma "Tor Vergata", Rome (IT)

( * ) Notice: Subject to any disclaimer, the term of this patent is extended or adjusted under 35 U.S.C. 154(b) by 1989 days.

(21) Appl. No.: 10/554,423

(22) PCT Filed: Apr. 19, 2004

(86) PCT No.: PCT/IT2004/000223
§ 371 (c)(1),
(2), (4) Date: Oct. 24, 2005

(87) PCT Pub. No.: WO2004/093874
PCT Pub. Date: Nov. 4, 2004

(65) Prior Publication Data
US 2006/0247284 A1    Nov. 2, 2006

(30) Foreign Application Priority Data

Apr. 24, 2003 (IT) .............................. RM2003A0194

(51) Int. Cl.
*A01N 43/82* (2006.01)
*A61K 31/41* (2006.01)
*A61K 45/06* (2006.01)
*A61K 31/4245* (2006.01)

(52) U.S. Cl.
CPC ............. *A61K 45/06* (2013.01); *A61K 31/4245* (2013.01)
USPC ........................................................ 514/364

(58) Field of Classification Search
CPC ........................... A61K 31/4184; C07D 271/08
USPC ........................................................ 514/364
See application file for complete search history.

(56) References Cited

PUBLICATIONS

Suggitt and Bibby, Clinical Cancer Research, 2005, vol. 11, 971-981.*
Whitehouse M W et al: "4-nitrobenzofurazans and 4-nitrobenzofuroxans: a new class of thiol-neutralising agents and potent inhibitors of nucleic acid synthesis in leucocytes." Biochemical Pharmacology. Jan. 1968, vol. 17, No. 1, Jan. 1968, pp. 158-161, XP002294567 ISSN: 0006-2952 p. 158, paragraph 1 p. 160, paragraphs 1,3; table 1.
Ghosh P B et al: "Potential antileukemic and immunosuppressive drugs. Preparation and in vitro pharmacological activity of some benzo-2,1,3-oxadiazoles (benzofurazans) and their N-oxides (benzofuroxans)." Journal of Medicinal Chemistry, Mar. 1968, vol. 11, No. 2, Mar. 1968 pp. 305-311, XP002294568 ISSN: 0022-2623 p. 305, col. 1, paragraph 1 p. 308, col. 2, paragraph 2; table 2.

* cited by examiner

*Primary Examiner* — Benjamin Packard
(74) *Attorney, Agent, or Firm* — Young & Thompson

(57) ABSTRACT

Derivatives of the heterocyclic compound known as 7-nitrobenzofurazan or 7-nitro-2,1,3-benzoxadiazole, are agents having a strong inhibiting activity towards members of the glutathione S-transferase (GST) superfamily that are hyperexpressed in cancer cells, and make them particularly resistant to many stress factors. These compounds are useful in the production of pharmaceutical drugs to be used in anticancer therapy, and may be employed either alone or in combination with other chemotherapeutic agents.

20 Claims, 6 Drawing Sheets

Caspase activity in cells treated with deivative No. 2 . ■ -
Apoptosis in cells treated with derivative No. 2: □ - Caspase
activity in control cells: ● - Apoptosis in control cells: ○

A     K562

B    Immunoprecipitation

C     CEM1.3

USE OF 7-NITRO-2,1,3-BENZOXADIAZOLE DERIVATIVES FOR ANTICANCER THERAPY

The present invention concerns the use of derivatives of 7-nitro-2,1,3-benzoxadiazole for anticancer therapy. More specifically, the invention refers to the use of derivatives of the heterocyclic compound known as 7-nitro-benzofurazan or 7-nitro-2,1,3-benzoxadiazole, as agents having a strong inhibitory activity towards the large family of glutathione S-transferases (GSTs), that are highly expressed in cancer cells and make such cells particularly resistant to many stress factors. These compounds are thus useful in the production of drugs for anticancer therapy and can be used either alone or in combination with other chemotherapy agents.

As is known, most anticancer drugs used in oncological treatment in the twentieth century consist of molecules which are not selective for cancer cells and are thus highly toxic for the body. The typical anticancer drugs include as widespread members the alkylating agents, which can non-selectively modify DNA and RNA, and the antimetabolites which, by mimicking the bases of DNA and of other natural molecules, interfere with the synthesis of nucleic acids, proteins and with other vital metabolic processes, acting as antagonists and inhibitors.

Oncological research has always tried to find drugs that could as selectively as possible inhibit the growth of cancer cells without interfering with normal cells. For this reason, oncological research has focused, for example, on the molecules which inhibit key enzymes for the survival of transformed cells.

These molecules include the inhibitors of telomerase, an enzyme whose activity allows cancer cells to continue dividing for a longer time span compared to the survival period of normal cells, and thus makes them "immortal". Other important target enzymes are the tyrosine-kinase, involved in the onset of cancer and of other proliferative diseases such as psoriasis and atherosclerosis. Another important research line focuses on developing specific inhibitors of farnesyl transferase, an essential enzyme for triggering protein p21, which is involved in cell proliferation and in neoplastic transformation.

Another key enzyme in signal transduction is the protein-kinase C (PKC), which is directly involved in the proliferation and differentiation processes and in the regulation of the MDR phenotype. Various natural inhibitors of PKC are known, and they are the rationale in new drug development.

A further class of target enzymes concerns the enzymes which regulate the cell cycle, particularly the cyclin-dependent kinases (CDK), whose inhibitors cause a cell cycle block in many cancer cell lines and may thus be used as cytostatics and as cytotoxics.

One enzyme that has been arousing much interest over the last few years in the oncological field is glutathione S-transferase (GST, EC 2.5.1.18). This is actually a family of isoenzymes that are widely found in nature and which catalyse the nucleophilic attack of the sulphur atom of glutathione (GSH) on electrophilic groups of substrate molecules. As is known, glutathione is a tripeptide composed of glutamic acid, cysteine and glycine, and is the most important low molecular weight compound found in animal or plant cells containing the thiol group. The glutathione S-transferases catalyse the conjugation of glutathione with many different types of xenobiotics, thus drastically reducing their reactivity and making these compounds more hydrosoluble, so as to favour their elimination.

On the basis of this mechanism, GST activity has been considered one of the factors responsible for the drug-resistance phenomenon seen in cancer cells, since many anticancer drugs are recognised as substrates by these enzymes (*Crit. Rev. Biochem. Mol. Biol.* 25, (1990), 47-70; *Crit. Rev. Biochem. Mol. Biol.* 30, (1995), 445-600; *Cancer Cells Mon. Rev.* 2, (1990), 15-22; *Cancer Res.* 54, 4313-4320; *Eur. J. Cancer* 32A, (1996), 967-978). GST is highly expressed in many human cancers and plays a key role in the detoxification of various anticancer drugs or their metabolites used in oncological treatment. The enzyme performs the glutathione conjugation of anticancer drugs such as nitrogen mustards, chlorambucil, cyclophosphamide, mitoxantrone and antraquinone, and could detoxify other drugs by not acting directly on the molecules but on a metabolite thereof.

GSTs constitute a multigenic family of isoenzymes that have been subdivided, according to their immunogenicity and primary structure, into at least ten classes, including Alpha, Pi and Mu. The enzymatic class hyperexpressed in greater amounts in cancers is Pi (GST-Pi), as observed in various human cancerous and precancerous tissues (*Mol. Pharmacol.* 50, (1996), 149-159). This increase in enzyme expression has been found both in cell lines resistant to alkylating agents (*Cancer Res.* 49, (1989), 6185-6192; *Br. J. Cancer,* 74, (1996), S93-S98), and in cancer cell lines resistant to doxorubicin and cisplatin (*Cancer Res.* 49, (1989), 7020-7025; *Cancer* 78, 1996, 416-421; *J. Biol. Chem.* 261, (1986), 15544-15549), and has also suggested the use of the Pi class GST enzyme as a cancer marker for its early diagnosis.

Moreover, many studies clearly show that GST hyperexpression in tumour makes anticancer drugs resistant not only through conjugation with glutathione, but also through other mechanisms still not fully clarified. A correlation has recently been found between the quantity of Pi class GST transferred in the nucleus of cancer cells and the resistance gained by these cells to drugs such as doxorubicin and cisplatin, and it has been hypothesised that Pi class GST in the nucleus protects DNA from damage caused by chemotherapy (*Faseb J.* 15, (2001), 2702-2714).

A great deal of evidence shows that GSTs also play an active role in controlling the process of programmed cell death (apoptosis). In cell stress conditions, such as after treatment with UV radiation or oxidizing agents, the protein-kinase c-Jun N-terminal (JNK) is activated, which is involved in mammal cell response to stress by regulating the cell cycle, repairing the DNA or inducing apoptosis. Recently, a protein inhibitor of JNK has been purified, identified as Pi class GST (*J. Biol. Chem.* 276, (2001), 20999-21003). This protein links up, through the region comprising the residues 194-201, to the Cterminal portion of the protein-kinase JNK, and it is known that factors causing cell stress involve the dissociation of the GST Pi/JNK complex and thus kinase activation.

In line with these results, it has also been found that specific inhibitors of GST Pi, such as the glutathione peptidomimetics TER-117 [Terrapin 117: γ-L-glutamyl-S-(benzyl)-L-cysteinyl-R-(−)-phenilglycine] and TER-293, trigger the protein-kinase JNK because they favour the dissociation of GST Pi from the GST Pi/JNK complex (*EMBO J.* 18, 1999, 1321-1334; J. Biol. Chem. 276, (2001), 20999-21003).

It has also been noted that GSTM1-1, a glutathione S-transferase belonging to the Mu class, binds with the N-terminal portion of another kinase that regulates the apoptotic signal, called ASK1 (apoptosis-signal-regulating kinase), inhibiting its activity. It has been shown that a thermal shock, causing the dissociation of the GSTM1-1/ASK1 complex, enables triggering ASK1. This kinase is in turn involved in a cascade of activation reactions of other proteins and phosphorylates JNK and kinase p38, that are known mediators of cell response to stress factors (*J. Biol. Chem.* 276, 2001, 12749-12755; *J. Biol. Chem.* 277, (2002), 30792-30797).

In conclusion, one of the main roles of GST appears to be that of down-regulating the cascade of signals linked to JNK through multiple mechanisms: the GST Mu enzyme acts on the ASK1 kinase and thus indirectly on JNK, while the GST Pi enzyme acts directly on JNK.

The aforesaid observations show that the hyperexpression of GST in cancer cells represents a protection mechanism for the latter against stress factors of the endogenous kind and those caused by anticancer drugs. Hence, cancer cells can acquire a resistance to these drugs and may no longer respond to apoptotic stimuli.

In view of the above, the search for efficient GST inhibitors has become one of the primary aims in order to modulate cancer cell resistance to anticancer drugs.

One of the first inhibitors of GSTs used was ethacrynic acid, an active principle long used as a diuretic (that has been recently replaced by furosemide for this indication), that sensitises cancer cells to the cytotoxic effect of alkylating agents. Although recognised as a substrate of some isoenzymes of GST, ethacrynic acid also behaves as an inhibitor of these enzymes. In this context, appreciable results have been obtained by using ethacrynic acid to lower the resistance of cancer cells to melfalan, carmustine, mitomycin C, doxorubicin and, to a lesser extent, to chlorambucil in patients affected by chronic lymphoblastic leukaemia (*Advanced Drug Delivery Reviews* 26, (1997), 91-104).

The lack of specificity as regards GST isoforms hyperexpressed in malignant cells, as well as a certain number of considerable side effects, such as a marked diuresis, have discouraged the use of ethacrynic acid in clinical practice, and some selective inhibitors for specific enzymatic GST classes have thus been introduced as an alternative (*Advanced Drug Delivery Reviews*, loc. cit.).

These are the aforesaid glutathione peptidomimetics, including, for example, TER 199 [γ-glutamyl-S-(benzyl)-cysteinyl-R(−)-phenilglicine diethylester] which rapidly enters cells and, being a pro-drug, is activated by the intracellular esterases. In the active form, the aforesaid drug TER-117, selectively inhibits the Pi class GSTs, enhancing the effect of the nitrogen mustards and generally of alkylating agents in various cancer cell lines such as those of the colon HT29 and those of the ovary carcinoma SKOV-3, which hyperexpress the isoenzyme GST Pi (*Cancer Chemother. Pharmacol.* 37, (1996), 363-370).

In both the ethacrynic acid and TER 199 cases, the sought action consists of enhancing the effect of other cytotoxic agents (alkylating agents) on resistant cancer cells. A different class of cytotoxic agents based on substances analogous to glutathione (*Advanced Drug Delivery Reviews*, already cited) consists of molecules that do not inhibit GST but exploit its catalytic power in order to be activated. These pro-drugs differ for their selectivity towards the various isoenzymes and for the various activated agents that derive from them. An example is TER 286, whose structure has the GST binding capacity of a GSH-peptidomimetic substance and the cytotoxicity of an alkilating nitrogen mustard. When activated by isoenzymes of the Pi and Alpha classes, the latent cytotoxin TER 286 releases an analogue of cyclophosphamide with inherent cytotoxic activity.

The present invention thus concerns the sphere of research into new selective inhibitors for the enzymatic classes of glutathione S-transferase hyperexpressed in cancer cells, in order to provide derivatives active as anticancer agents, both for their intrinsic cytotoxic power and for their ability to inhibit the detoxification activity of GSTs towards other chemotherapeutic agents.

As previously noted, some GST classes are hyperexpressed in many cancer cells, so much so that some isoforms, such as GSTP1-1, belonging to the GST Pi class, can be used as tumor markers. This enzymatic hyperexpression, documented for most cancers, makes cancer cells drug-resistant not only for the detoxifying activity that these enzymes catalyse, but also through the anti-apoptotic activity they show, interfering in the signal transduction mechanisms that regulate apoptosis.

In the studies the lead to the present invention, it was found that some specific derivatives of 7-nitro-2,1,3-benzoxadiazole show—in various cancer cell lines—considerable selective inhibition activity towards the GST isoforms considered, as well as a high cytotoxic power. These molecules selectively bind to the hydrophobic site of the GSTs (where the co-substrate that must be conjugated to glutathione is bound) and strongly inhibit the activity of these isoenzymes.

The derivatives of 7-nitro-2,1,3-benzoxadiazole that have been considered according to the present invention can easily be prepared starting from 4-chloro-7-nitro-2,1,3-benzoxadiazole, a fluorogenic molecule well-known in biochemistry, used for marking thiol and amine compounds (*FEBS Lett.* 6, (1970), 346-348; *Eur. J. Biochem.* 54, (1975), 117-126; *Eur. J. Biochem.* 54, (1975), 127-133). 4-chloro-7-nitro-2,1,3-benzoxadiazole is well recognized as a co-substrate by the GST of class Alpha, but it is also used as a substrate by the Pi and Mu GSTs, generating the product, i.e. (7-nitro-2,1,3-benzoxadiazol-4-ylthio)glutathione (*Anal. Biochem.* 218, (1994), 463-465; *J. Biol. Chem.* 271, (1996), 16193-16198). The latter molecule is a good GST inhibitor, but enters the cells with difficulty and is rapidly expelled by them.

The derivatives of 7-nitro-2,1,3-benzoxadiazole (also called 4-nitrobenzofurazan) had already received attention in the past for their possible clinical applications as anticancer drugs. The initial studies on compounds of this family date back to the late 1960s, with some publications that highlight their potential antileukaemic activity (*Biochemical Pharmacology* 17, (1968), 158-161; *J. Med. Chem.* 11, (1968), 305-311). These publications concern a limited number of 7-nitro-2,1,3-benzoxadiazole derivatives, and report their activity in inhibiting uridine-5-$^3$H incorporation into sheep lymphocyte RNA in vitro, i.e. in inhibiting the lymphocyte metabolism. Later studies found that 7-phenylthio- and 7-purine-6-thio-4-nitrobenzofurazan are powerful inhibitors of the synthesis of nucleic acids and proteins in some normal and cancer mammalian cell lines (*Chem. Biol. Interactions* 42, (1982), 195-207). The overall results obtained in these works are contradictory, and this research line does not seem to have been further prosecuted.

On the other hand, the present invention proposes the use, as inhibitors of GSTs and anticancer agents, of specific derivatives of 7-nitro-2,1,3-benzoxadiazole that are not mentioned as possible anticancer agents in previous studies.

The derivatives of 7-nitro-2,1,3-benzoxadiazole that are the object of the present invention are characterised by the presence of a tioether bridge in position −4, and by the presence of an aliphatic group with characteristics of a bad leaving group connected thereto. The latter also contains, preferably, at least one —OH group. Said derivatives have the capacity to quickly enter cancer cells, where they carry out a remarkable cytotoxic activity. This action is likely due to the inhibition of the detoxifying activity (as demonstrated by specific experimental evidence obtained in vitro on purified isoenzymes) and anti-apoptotic activity of the GSTs, particularly of the isoform GSTP1-1 which is hyperexpressed in cancer cell lines. Thus, the use of the derivatives according to the present invention makes it possible to carry out a treatment aimed at obtaining a cytotoxic effect on cancer cells—the primary targets of these highly selective compounds—interfering less effectively with the physiology of normal cells.

As concerns the chemical structure of the compounds according to the present invention, it must be noticed that the nature of the leaving groups present in their skeleton results in slow or null exchange reactions with endogenous thiols such as glutathione and in the formation of a stable σ-adduct with GSH, as shown in the experimental section herein. The exchange reactions with endogenous thiols is a documented phenomenon in the case of other derivatives of 7-nitro-2,1,3-benzoxadiazole studied in the aforesaid previous research line. In the course of the aforesaid previous experiments some of the —O—, —NR— and —S— derivatives of 7-nitro-2,1,3-benzoxadiazole were tested, and, in particular, among the —S— derivatives, compounds were tested where the group binding with sulphur in position –4 is alternatively a phenyl, benzyl, acetyl or a cyano group. The modest and contradictory results described are to be ascribed to the presence—in these compounds—of good leaving groups such as chlorine, thiocyanate, phenoxy-, phenylthio- and benzylthio-. These groups favour exchange reactions with glutathione, leading to the formation of adducts with the latter. These adducts are preferably expelled by the cells through specific membrane glycoproteins belonging to the family of proteins involved in the process of drug-resistance to several agents (multidrug resistance protein, MRP) (*Free Rad. Biol. Med.* 27, (1999), 985-991).

Moreover, as already noted, some of the compounds described in the cited literature present considerable solubility problems that compromise the possibility of in vivo administration. On the other hand, in derivatives of 7-nitro-2,1,3-benzoxadiazole, according to the present invention, the presence of at least one —OH group contributes to providing these compounds with a good solubility in an aqueous medium, while still maintaining a degree of apolarity such as to allow interaction with the hydrophobic binding site of the GSTs substrate, and to express their strong enzymatic inhibition activity.

Outside the oncological field, some applications of 7-nitro-2,1,3-benzoxadiazole derivatives functionalised in –4 through a thioether bridge are already known, for example as fluorescent reactives in the study of the metabolism of some thiol inhibitors in the conversion of angiotensin I to angiotensin II (U.S. Pat. No. 4,395,556 and No. 4469870), and generally as fluorescent probes for marking nucleic acids or proteins. Other 4-S— derivatives of 7-nitro-2,1,3-benzoxadiazole are described in US patent application No. 2002/0189032 and EP-A-1261591, where they are proposed for use as colorants of keratin fibres and in particular for hair.

Therefore, the present invention specifically provides the use of derivatives of 7-nitro-2,1,3-benzoxadiazole of general formula (I),

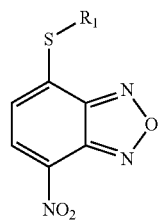

wherein:
$R_1$ is chosen from the group consisting of linear, branched or cyclic alkyl with up to 12 carbon atoms, linear, branched or cyclic alkenyl with up to 12 carbon atoms, linear, branched or cyclic alkynyl with up to 12 carbon atoms,
one hydrogen atom of $R_1$ being optionally substituted with one group chosen from the groups consisting of $OR_2$, $NO_2$, $NR_2R_3$,
wherein $R_2$ and $R_3$ are independently chosen from the group consisting of H, linear, branched or cyclic alkyl, alkenyl or alkynyl with up to 12 carbon atoms, and wherein said S—$R_1$ group is not a good leaving group,
for the preparation of a GST-inhibiting medicament for the treatment of cancer forms. According to the present invention, the above GST selective inhibitors can be advantageously employed in antineoplastic therapies, by administering them alone as cytotoxic agents or in combination with other chemotherapeutic agents in order to enhance the therapeutic effect thereof by reducing, the drug-resistance effect.

According to some specific embodiments thereof, the present invention concerns the use of derivatives of 7-nitro-2,1,3-benzoxadiazole of the general formula (I), where $R_1$ is a linear or branched hydroxyalkyl with up to 12 carbon atoms, and is preferably chosen from 4-hydroxybutyl and 6-hydroxyhexyl. The preferred active ingredients for the proposed use according to the present invention correspond to one of the following:
4-(7-nitro-2,1,3-benzoxadiazol-4-ylthio)butanol
6-(7-nitro-2,1,3-benzoxadiazol-4-ylthio)hexanol.

According to a further aspect thereof, the present invention more specifically refers to the use of derivatives of 7-nitro-2,1,3-benzoxadiazole of the general formula (I) for the treatment of various cancer forms, and particularly those forms characterised by a GST hyperexpression. The aforesaid enzyme isoforms, which are hyperexpressed in solid tumours, lymphomas and in leukaemias, can belong to the GST Pi, GST Mu and GST Alpha classes of glutathione S-transferase, and more specifically can be the isoforms GSTP1-1, GSTM2-2 and GSTA1-1.

A further specific object of the present invention is a pharmaceutical composition for the treatment of cancer including—as an active ingredient—at least one of the 7-nitro-2,1,3-benzoxadiazole derivatives of the general formula (I), together with one or more pharmacologically acceptable adjuvants and/or vehicles.

The suitable pharmaceutical preparations for the therapeutic administration of GST inhibitors, according to the present invention, can be formulated on the basis of conventional techniques known to those skilled in the art, by using pharmaceutically acceptable eccipients and vehicles in order to obtain preparations suitable for parenteral injection (intravenous, intramuscular or subcutaneous injection), for oral administration in solid or liquid form, for transdermal, rectal, intravaginal or local administration, for example, on the oronasal tract mucous membranes and the like.

The percentage of active ingredient in the composition and the anticancer treatment method may be varied in order to obtain an optimal dosage. The dose to be administered takes the following factors into account: the administration route, the duration of treatment, the patient's weight and conditions, the activity of the active ingredient and the patient's responsiveness.

Once the proper dosage of the active ingredient has been determined, the formulation and choice of suitable excipients and adjuvants for every need may be made on the basis of common knowledge of the field.

Some experimental results obtained within the frame of the present invention, including the data relative to the biological activity and characteristics—as GST inhibitors—of some 7-nitro-2,1,3-benzoxadiazole derivatives of which the synthesis is also described, are reported below as examples. Some of the said experimental results are also shown in the graphs of the accompanying drawings, wherein.

Figure 3:
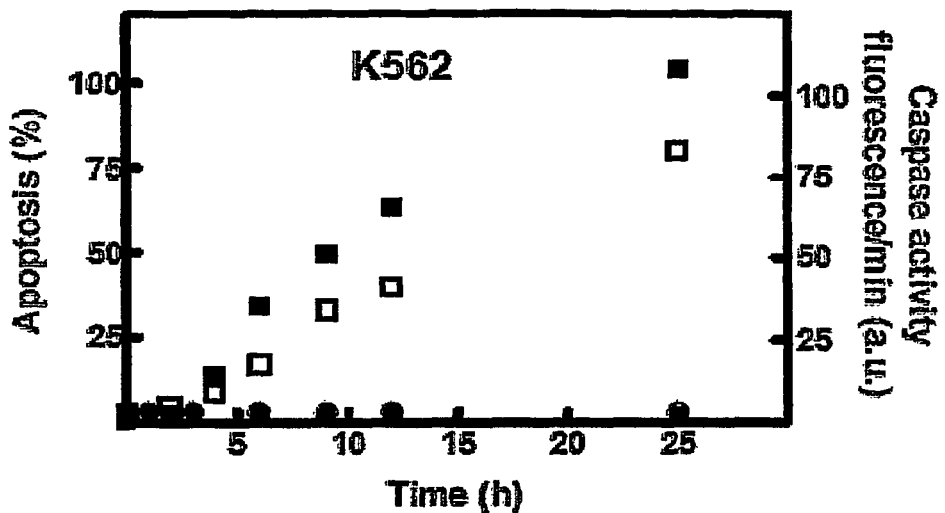
Figure 3:
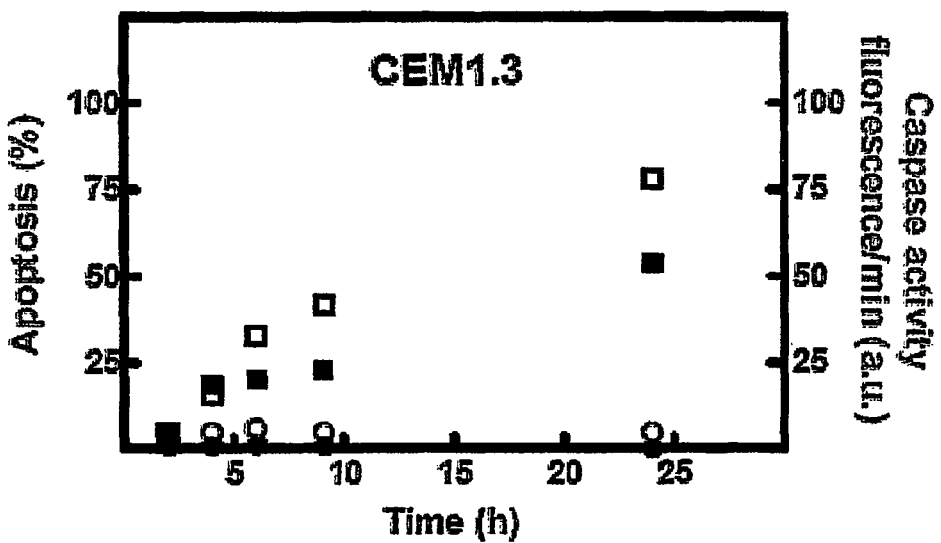
Figure 4:
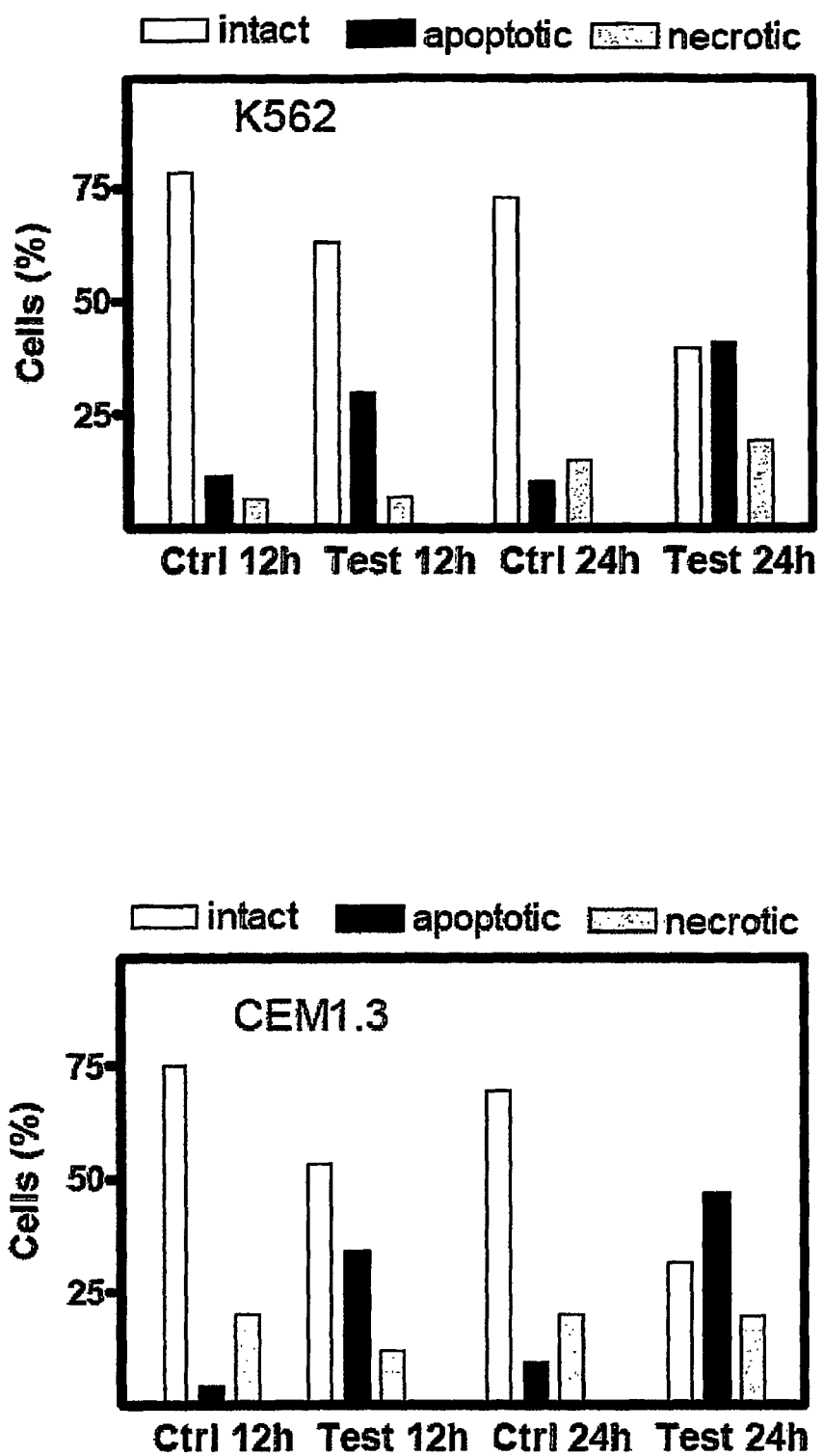
Figure 5:
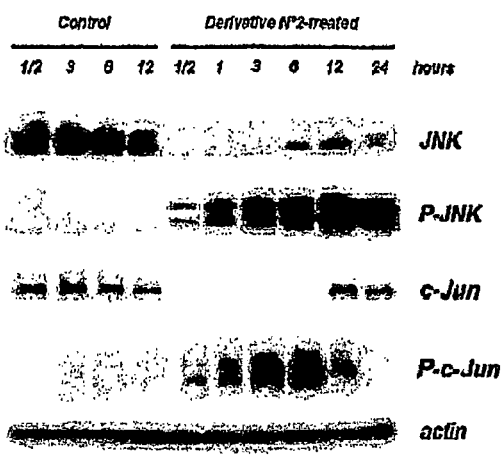
Figure 5:
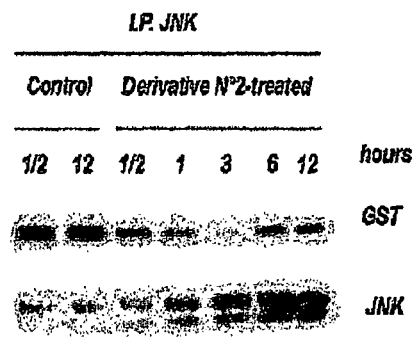
Figure 5:
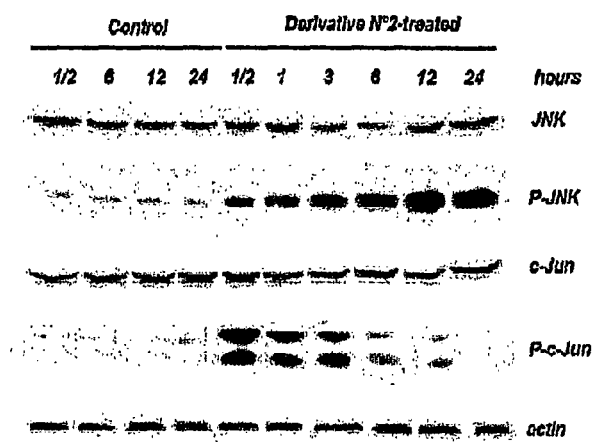
Figure 6:
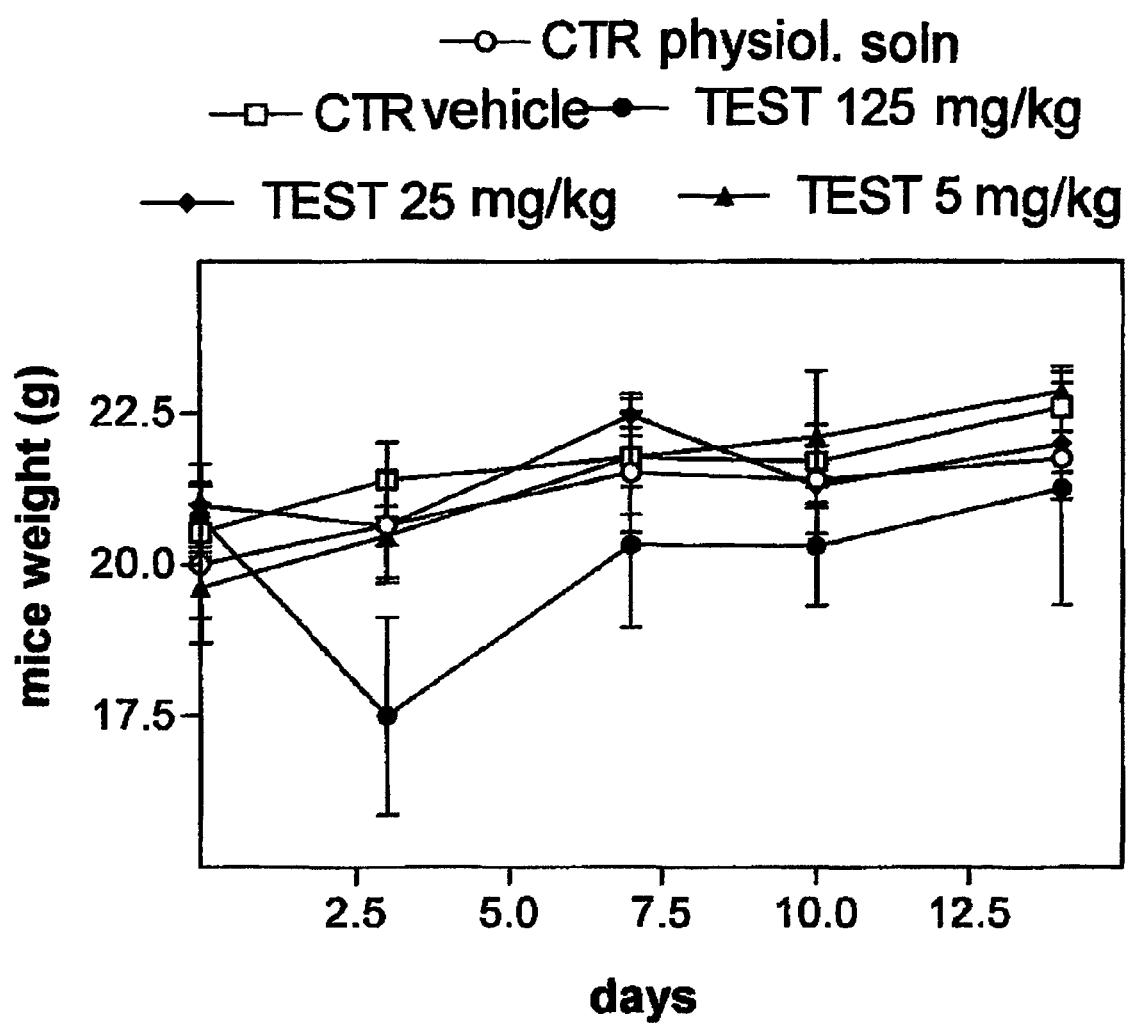

FIG. 3 shows the caspase-3 activity in CEM1.3 and K562 cell lines after treatment with 7-nitro-benzofurazan derivative No. 2 (■) and the caspase-3 activity in control cells (●); the percentage of apoptosis in CEM1.3 and K562 cell lines after treatment with 7-nitro-benzofurazan derivative No. 2 (□) and in control cells (○); activity was expressed as fluorescence change observed per minute per number of cells; apoptosis was determined by analyzing the nuclear fragmentation after cell staining with Hoechst 33342 dye;

FIG. 4 shows the results of flow cytometric analysis performed on K562 and CEM1.3 cell lines treated with 10 μM and 2 μM derivative No. 2 respectively; after 12 and 24 h treatment, cells were washed and stained with both Annexin V-FITC and PI, which allow the discrimination of intact cells, early apoptotic and late apoptotic or necrotic cells;

FIGS. 5 (A, B and C) shows Western blot analyses of K562 and CEM1.3 cell lines treated with 10 μM and 2 μM derivative No. 2 respectively; GSTP1-1, c-Jun, JNK and the phospho-activated c-Jun and JNK isoforms were detected by specific antibodies; β-actin was used as loading control (Panels A and C); dissociation of GST/JNK complex was evaluated by immunoprecipitation analysis; lysates were immunoprecipitated using anti-JNK polyclonal antibody and then subjected to Western blot analyses; GST and JNK were detected by specific antibodies (Panel B); and FIG. 6 shows the weight variations of mice in an in vivo acute toxicity test comparing the effect of parenteral administration of different dosages of the test compound No. 2 of the invention, in comparison with controls receiving physiological solution or the vehicle only.

As regards the synthesis, as already noted, the derivatives forming the object of the present invention, as well as the compounds to be used for comparison, may be prepared starting from a readily available initial compound, 4-chloro-7-nitro-2,1,3-benzoxadiazole (Sigma-Aldrich, Fine Chemicals), without ruling out alternative synthesis methods.

EXAMPLE 1

4-(7-nitro-2,1,3-benzoxadiazol-4-ylthio)butanol

A mixed solution of 4-chloro-7-nitro-2,1,3-benzoxadiazole (1 mmole) and of 4-mercapto-1-butanol (Sigma-Aldrich, Fine Chemicals) (2 mmoles) was made to react in 20 ml of ethanol: 1:1 potassium phosphate buffer, at pH 7.0 for 6 hours in a closed beaker, at 25° C. The pH was continuously monitored to keep it neutral by adding small quantities of KOH. At the end of the reaction, the excess 4-mercapto-1-butanol was made to react with 1.5 mmoles of 3-bromopyruvate.

The reaction product, 4-(7-nitro-2,1,3-benzoxadiazol-4-ylthio)butanol, is a dark yellow insoluble compound that is collected by filtering and washed twice with 15 ml of cold distilled water. The final product is seen to be 98% pure via HPLC analysis.

The molecular weight of the compound determined by mass spectrometry is 269 Da.

The UV spectrum visible in water is characterised by a maximum absorption peak at 431 nm ($\epsilon=15$ mM$^{-1}$ cm$^{-1}$) and the fluorescence spectrum in water shows a maximum emission peak at 525 nm.

EXAMPLE 2

6-(7-nitro-2,1,3-benzoxadiazol-4-ylthio)hexanol

A mixed solution of 4-chloro-7-nitro-2,1,3-benzoxadiazole (1 mmole) and of 6-mercapto-1-hexanol (Sigma-Aldrich, Fine Chemicals) (2 mmoles) was made to react in 20 ml of ethanol: 1:1 potassium phosphate buffer, at pH 7.0 for 6 hours in a closed beaker, at 25° C. The pH was continuously monitored to keep it neutral by adding small quantities of KOH. At the end of the reaction, the excess 6-mercapto-1-exanol was made to react with 1.5 mmoles of 3-bromopyruvate.

The reaction product, 6-(7-nitro-2,1,3-benzoxadiazol-4-ylthio)hexanol, is a dark yellow insoluble compound that is collected by filtering and washed twice with 15 ml of cold distilled water.

The final product is seen to be 98% pure via HPLC analysis. The molecular weight of the compound determined by mass spectrometry is 298 Da.

The visible UV spectrum is characterised by a maximum absorption peak at 432 nm ($\epsilon=15$ mM$^{-1}$ cm$^{-1}$) and the fluorescence spectrum shows a maximum emission peak at 525 nm.

EXAMPLE 3

2-(7-nitro-2,1,3-benzoxadiazol-4-ylthio)imidazole

A solution of 4-chloro-7-nitro-2,1,3-benzoxadiazole (1 mmole) and 2-mercaptoimidazol (Sigma-Aldrich, Fine Chemicals) (1 mmole) was made to react in 6 ml of ethanol: water 0.3:1, containing 2.5 mmoles of pyridine (Sigma-Aldrich, Fine Chemicals). After 1 hour of incubation at 25° C., the solution was filtered, washed twice with 10 ml of cold distilled water and dried under vacuum.

The insoluble product, 2-(7-nitro-2,1,3-benzoxadiazol-4-ylthio)imidazole, is an orange colour and is 98% pure on HPLC analysis. The molecular weight of the compound determined by mass spectrometry is 264 Da.

The compound has a visible UV spectrum characterised by a maximum absorption peak at 401 nm ($\epsilon=11.5$ mM$^{-1}$ cm$^{-1}$) and does not have a fluorescence emission spectrum.

EXAMPLE 4

4-(7-nitro-2,1,3-benzoxadiazol-4-ylthio)phenol

A mixed solution of 4-chloro-7-nitro-2,1,3-benzoxadiazole (1 mmole) and 4-mercaptophenol (Sigma-Aldrich, Fine Chemicals) (2 mmoles) was made to react in 20 ml of ethanol: 1:1 potassium phosphate buffer, at pH 7.0 for 6 hours in a closed beaker, at 25° C. The pH was kept neutral by adding small quantities of KOH. At the end of the reaction, the excess 4-mercaptophenol was made to react with 1.5 mmoles of 3-bromopyruvate.

The reaction product, 4-(7-nitro-2,1,3-benzoxadiazol-4-ylthio)phenol, was collected by filtering, washed twice with 15 ml of cold distilled water and dried under vacuum. The final product is a brown insoluble compound and is seen to be 98% pure via HPLC analysis. The molecular weight of the compound determined by mass spectrometry is 289 Da.

The compound has a water visible UV spectrum characterised by a maximum absorption peak at 428 nm ($\epsilon=11.5$ mM$^{-1}$ cm$^{-1}$) and does not have a fluorescence emission spectrum.

EXAMPLE 5

3-(7-nitro-2,1,3-benzoxadiazol-4-ylthio)propionic acid

A solution of 4-chloro-7-nitro-2,1,3-benzoxadiazole (1 mmole) and 3-mercaptopropionic acid (Sigma-Aldrich, Fine Chemicals) (1 mmole) was made to react in 6 ml of ethyl alcohol: water 0.3:1 containing 2.5 mmoles of pyridine.

After an hour of incubation at 25° C., the solution was filtered, washed twice with 10 ml of cold distilled water and then dried under vacuum. The insoluble reaction product, 3-(7-nitro-2,1,3-benzoxadiazol-4-ylthio)propionic acid, is a dark yellow colour and seen to be 98% pure on HPLC analysis. The molecular weight is 270 Da.

The compound has a water visible UV spectrum characterised by a maximum absorption peak at 428 nm ($\epsilon=12$ mM$^{-1}$ cm$^{-1}$) and the fluorescence spectrum shows a maximum emission peak at 525 nm.

Study of the Biological Activity of Glutathione S-Transferase Inhibition by the 7-nitro-2,1,3-benzoxadiazole Derivatives Experimental Procedure—

The 7-nitro-2,1,3-benzoxadiazole derivatives of Examples 1 and 2 were used, prepared according to the procedures described in the said examples. For comparison, the performances of the following compounds were also assessed:

the compounds of Examples 3 and 4, characterized by moderate leaving groups;

the compound of Example 5, characterized by a basically bad leaving group modified by the substitution of one hydrogen with a COOH group;

the derivative 6-(7-nitro-2,1,3-benzoxadiazol-4-ylamino) hexanol, where S is substituted by NH in the formula, the NHR$_1$ group not being a leaving group.

The latter acted as a control to ensure that the cytotoxicity is linked to GST inhibition. 6-(7-nitro-2,1,3-benzoxadiazol-4-ylamino)hexanol was obtained by reacting 1 mmole of 4-chloro-7-nitro-2,1,3-benzoxadiazole with 1 mmole of 6-amino-1-hexanol (Sigma-Aldrich, Fine Chemicals) in 6 ml of ethylic alcohol: water 0.3:1 containing 2.5 mmoles of pyridine.

These compounds were tested as inhibitors of the activity of the isoenzymes GSTP1-1, GSTA1-1 and GSTM2-2 belonging to the most representative GST classes: the Pi, Mu and Alpha classes.

GSTA1-1, M2-2 and P1-1, expressed in *Escherichia coli*, were purified by using a chromatographic passage on an affinity resin capable of selectively retaining the GST (J. Biol. Chem. 270, (1995), 1249-1253).

GST activity was tested at 25° C. with a 0.1 M potassium phosphate buffer, at pH 6.5, in the presence of the substrates, i.e. of the glutathione (Sigma-Aldrich, Fine Chemicals) in a concentration of 1 mM, and of 1-chloro-2,4-dinitrobenzene (CDNB) (Sigma-Aldrich, Fine Chemicals) 1 mM (*Methods Enzymol.* 77, 1981, 398-405).

During testing to determine the IC$_{50}$ (inhibitor concentration at which an inhibition of enzymatic activity of 50% is observed), the activity mixture was added with the various quantities of the 7-nitro-2,1,3-benzoxadiazole derivatives to be assayed.

Enzymatic activity was assessed spectrophotometrically at 340 nm, a wavelength at which it absorbs the reaction product S-(2,4-dinitrobenzene)glutathione (GS-DNB) ($\epsilon=9.6$ mM$^{-1}$ cm$^{-1}$).

Results—

The IC$_{50}$ ($\mu$M) values of the 7-nitro-2,1,3-benzoxadiazole derivatives are reported in Table 1 below. The table shows the IC$_{50}$ values for the various inhibitors tested with respect to the three representative isoenzymes of each GST class.

Each compound is given in the table with a number corresponding to the relative synthesis example, while the comparison amine derivative is given with the number 6.

TABLE 1

| Inhibition of GST activity - IC$_{50}$ values ($\mu$M) | | | |
| --- | --- | --- | --- |
| | Enzyme | | |
| Compound No. | GST A1-1 | GST P1-1 | GST M2-2 |
| (1) | 56.00 | 2.00 | 0.03 |
| (2) | 25.00 | 0.80 | 0.01 |
| (3) | 11.00 | 6.30 | 0.01 |
| (4) | 6.50 | 0.70 | 0.03 |
| (5) | 66.00 | 5.74 | 0.31 |
| (6) | >100 | ≥100 | 1.80 |

(1) 4-(7-nitro-2,1,3-benzoxadiazol-4-ylthio)butanol
(2) 6-(7-nitro-2,1,3-benzoxadiazol-4-ylthio)hexanol
(3) 2-(7-nitro-2,1,3-benzoxadiazol-4-ylthio)imidazole
(4) 4-(7-nitro-2,1,3-benzoxadiazol-4-ylthio)phenol
(5) 3-(7-nitro-2,1,3-benzoxadiazol-4-ylthio)propionic acid
(6) 6-(7-nitro-2,1,3-benzoxadiazol-4-ylamino)hexanol As already noted, the inhibiting capacity towards the various GST isoenzymes of the 6-(7-nitro-2,1,3-benzoxadiazol-4-ylamino)hexanol derivative was also tested. The sulphur atom in the latter formula is substituted by an amine group in order to assess whether the cytotoxicity is linked to GST inhibition.

The analysis of these initial data shows that the compound has practically lost its capacity to inhibit GSTP1-1 (IC$_{50}$≥100

μM) but maintains a higher inhibiting capacity as regards GSTM2-2 with an $IC_{50}$ of 1.8 μM.

For the analogous inhibitor whose formula includes sulphur, there is a much lower $IC_{50}$ (greater inhibiting capacity) with respect to the control, and namely 0.80 μM for GSTP1-1 and 0.01 μM for GSTM2-2.

Mechanism of the Interaction Between 7-nitro-benzofurazan Derivatives and GSTs

Binding of 7-nitro-benzofurazan Derivatives to GSTs

Experimental Procedure—

Affinity of 7-nitro-benzofurazan derivatives to human GSTs was obtained by measuring the quenching of the intrinsic fluorescence of the protein that occurs after the inhibitors binding (excitation was at 295 nm and emission was recorded at 340 nm). The intrinsic fluorescence was measured in a single photon counting spectrofluorometer (Fluoromax, S.A. Instruments, Paris, France). In a typical experiment fluorescence at 340 nm was recorded before and after the addition of variable amounts of a selected inhibitor to 4 μM GST in 0.1 M K-phosphate buffer pH 6.5 containing 1 mM GSH.

Results—

Figure 1:
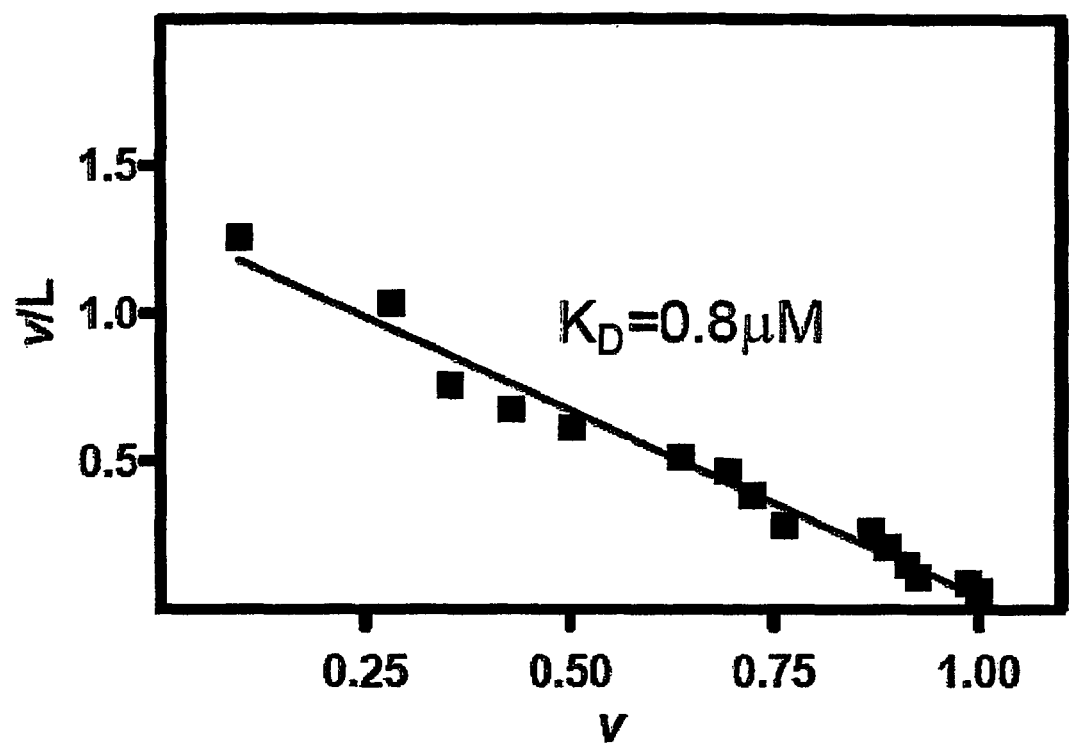
FIG. 1 shows a Scatchard plot for the binding of the 7-nitro-benzofurazan derivative referred to as No. 2 in the following (6-(7-nitro-2,1,3-benzoxadiazol-4-ylthio)hexanol) to GSTP1-1; in the graph, ν is the ratio between the fluorescence change observed at a given ligand concentration and the fluorescence change observed at saturating ligand concentration; L is the free ligand concentration.

Representative data obtained with GSTP1-1 and 7-nitro-benzofurazan derivative No. 2 (synthesis example 2) are presented as Scatchard plot in FIG. 1. The dissociation constant obtained for the inhibitorGSTP1-1 complex is $K_D$=0.8 μM, which superimposes on the $IC_{50}$ value obtained kinetically and reported in Table 1. It is remarkable that GSH is essential for a good affinity between the 7-nitro-benzofurazan derivative and GST: in fact, in the absence of GSH, the affinity decreases of about two orders of magnitude.

Spectroscopic Evidence for σ-Adduct Formation at the Active Site

Experimental Procedure—

UV-visible spectrum of 15 μM 7-nitro-benzofurazan derivative No. 2 in the presence of stoichiometric amounts of GSTP1-1 and GSH 1 mM was obtained at 25° C. in 0.1 M K-phosphate buffer pH 6.5.

Results—

Figure 2:
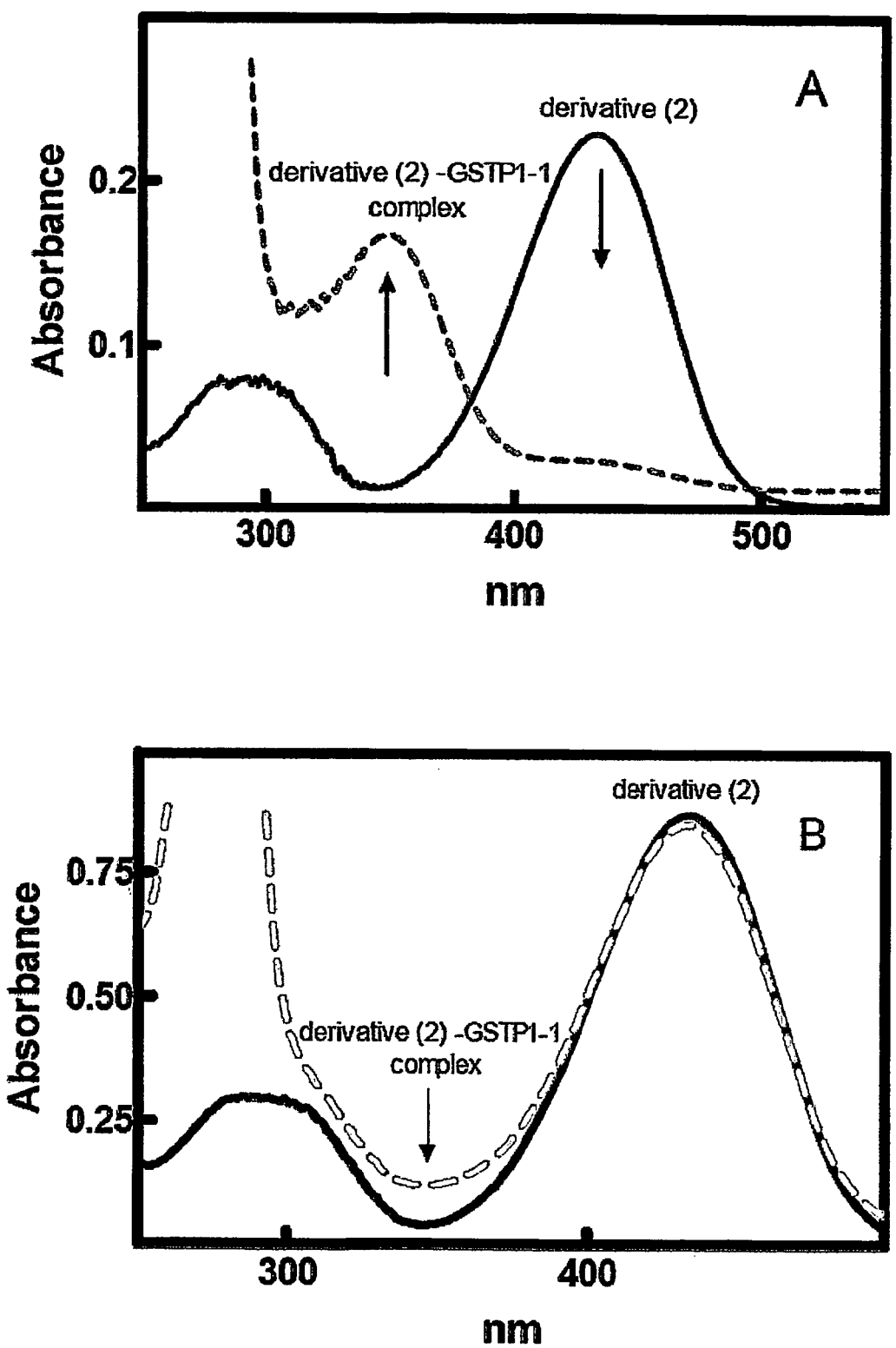
FIG. 2 shows the spectrum of 15 μM 7-nitro-benzofurazan derivative No. 2 in 0.1 M K-phosphate buffer, pH 6.5 (Panels A and B, continuous lines), and the spectrum of 15 μM 7-nitro-benzofurazan derivative No. 2 bound to stoichiometric amounts of GSTP1-1, in the presence of either 1 mM GSH (Panel A, dashed line) or 1 mM S-methylglutathione (Panel B, dashed line)

In the presence of GSTP1-1 and GSH, an immediate disappearance of the 432 nm band, typical of the 7-nitro-benzofurazan derivative, and a parallel increase of a band centred at 348 nm is observed (FIG. 2, Panel A). The thiol group of GSH is essential to obtain this spectral change. In fact, no change is observed in the UV-visible spectrum when 7-nitro-benzofurazan derivative (50 μM) is incubated with stoichiometric amounts of GSTP1-1 and 1 mM S-methylglutathione (FIG. 2, Panel B).

This behaviour can be explained by previous reports showing that 7-nitrobenzofurazans are excellent electrophiles, readily forming σ-adducts with many nucleophiles (*J. Chem. Soc.*, Perkin Trans 2, (2002) 257-261). The usual behaviour observed is a kinetically preferred attack of the nucleophile at the 6-position of the 7-nitrobenzofurazan ring, followed by a slow isomerization towards the more stable 4-adduct which absorbs between 300 and 400 nm. In the above experimental conditions the G-adduct can be formed by a covalent interaction between the 7-nitrobenzofurazan derivative and the thiol group of GSH bound at the GSTP1-1 active site, as reported in scheme A.

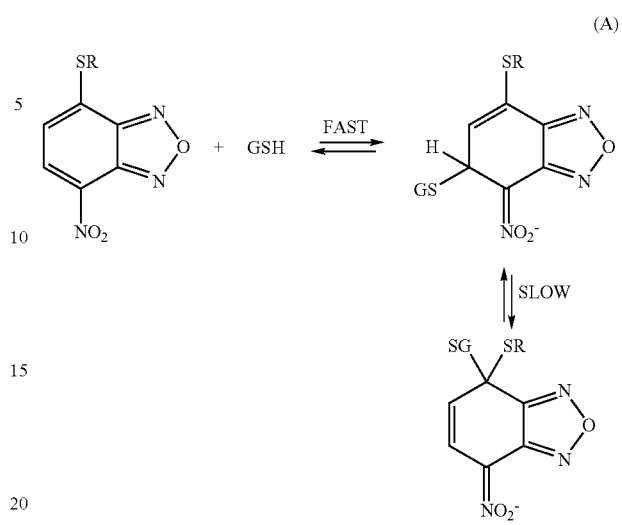

This hypothesis is in accordance with the docking approach performed to predict the ligand orientation into the GST binding site. Comparison between the binding energies for the σ-adduct at the 6-position and at the 4-position reveals a two order of magnitude stabilization of the 4-substituted compound.

From the above data it is evident that the real inhibitor species which inhibits GSTP1-1 is the σ-adduct formed between the 7-nitro-benzofurazan derivative and GSH. The GSTs are very efficient in catalysis of the σ-adduct formation between 7-nitro-benzofurazan derivatives and GSH. Bad leaving groups such as alkyl-thio groups may stabilize the σ-adduct by preventing the formation of the monosubstituted 4-glutathionyl-7-nitro derivative. Moreover, these σ-adducts are characterized by a negative charge localised on the 7-nitro group that can be specifically stabilized by the enzyme. In fact, in the absence of GSTP1-1, detectable amounts of σ-adduct are obtained in solution only at GSH concentrations higher than 5 mM, and the equilibrium constant calculated for this reaction is K=20 mM. Based on this equilibrium constant, the amount of σ-adduct formed with 1 mM GSH (GSH concentration utilized in our experiments) and in the absence of GSTP1-1 is about 5% of the 7-nitro-benzofurazan concentration. Therefore, the affinity of the GSTP1-1 towards the real inhibitor species becomes $4 \times 10^{-8}$ M. This strong affinity indicates that GSTP1-1 is a very selected target for this molecule inside the cell.

Assays on Cell Lines of the Anticancer Activity of Derivatives of 7-Nitro-2,1,3-benzoxadiazole Experimental Procedure—

Four cancer cell lines were used for testing the anticancer activity of the derivatives of 7-nitro-2,1,3-benzoxadiazole: K562 (human myeloid leukaemia), HepG2 (human hepatic carcinoma), CEM1.3 (human T-lymphoblastic leukaemia) and GLC-4 (human small cell lung carcinoma).

The human cancer cell lines were maintained in RPMI 1640 (containing L-glutamine 2 mM and 0.1 g/l of penicillin-G/streptomycin sulphate) enriched with 5% foetal bovine serum (FBS), at 37° C., 5% CO2 and 98% humidity.

The cells were placed in 96-well plates at a density of 15,000 cells per well, in a culture medium volume of 100 μl. After 24 hours, each of the 7-nitro-2,1,3-benzoxadiazole derivatives to be assayed, at the required concentration, was added to the culture medium. At the same time, some control trials were arranged by adding to the wells the solvent in which the compound was dissolved (% v/v of DMSO in PBS). All measurements were carried out in quadruplicate.

The cells were incubated for 48 hours at 37° C., at 5% $CO_2$.

In order to obtain a dose-response profile for each derivative of 7-nitro-2,1,3-benzoxadiazole under study, an evaluation process based on the method described by Shekan et al (*J. Natl. Cancer. Inst.* 82, (1990), 1107-1112) was used.

After incubation, the percentage cell growth was evaluated by an insitu cell fixation procedure, followed by an SRB test using a colouring procedure with sulphorodamine B capable of specifically binding to proteins. The coloured product was then solubilised and quantified spectrophotometrically in order to determine the growth of the cells treated with the compound under study with respect to the ones treated with the solvent only.

In order to also measure the activity of the endogenous GSTs present in the cells used, the same cancer cell lines were used: K562, HepG2, CEM1.3 and GLC-4. In this case, the culture cells were trypsinised as necessary, collected by centrifugation and washed twice in PBS. The cells were then resuspended in two volumes of PBS and lysated by sonication. The cell lysate was centrifuged at 15,000 g for 15 minutes. The supernatant was collected and used for the enzymatic testing of the GSTs described in the previous example.

One unit of GST is defined as the quantity of enzyme that catalyses the formation of 1 pmole of product (GS-DNB) per minute at 25° C.

Protein concentration was determined by using the bicinconinic acid method (Pierce).

Results—

The $IC_{50}$ values (the concentration of compound at which a 50% inhibition of cell growth is observed with respect to untreated cells) expressed in μM, of the 7-nitro-2,1,3-benzoxadiazole derivatives are reported in Table 2.

The compounds listed in Table 2 have been given the same numbering sequence as the ones used in the experimentation reported above. As in the previous experimentation, compounds (3)-(6) are presented for comparison with the claimed compounds (1) and (2).

TABLE 2

Activity trials on cell lines - $IC_{50}$ values (μM)

| Compound No. | Cell line | | | |
|---|---|---|---|---|
| | CEM1.3 | GLC-4 | K562 | HepG2 |
| (1) | 0.2 | 3.2 | 2.2 | 3.2 |
| (2) | 0.1 | 1.4 | 0.8 | 2.9 |
| (3) | 3.9 | 10 | 8.8 | 16 |
| (4) | 2.4 | 7.5 | 6.4 | 16.3 |
| (5) | 6.5 | 16.5 | 38 | 25 |
| (6) | >50 | >50 | >50 | >50 |

(1) 4-(7-nitro-2,1,3-benzoxadiazol-4-ylthio)butanol
(2) 6-(7-nitro-2,1,3-benzoxadiazol-4-ylthio)hexanol
(3) 2-(7-nitro-2,1,3-benzoxadiazol-4-ylthio)imidazole
(4) 4-(7-nitro-2,1,3-benzoxadiazol-4-ylthio)phenol
(5) 3-(7-nitro-2,1,3-benzoxadiazol-4-ylthio)propionic acid
(6) 6-(7-nitro-2,1,3-benzoxadiazol-4-ylamino)hexanol On the basis of the SRB test, the 7-nitro-2,1,3-benzoxadiazole derivatives according to formula (1) show an excellent cytotoxic activity. The $IC_{50}$ values obtained on the cell lines are of the same magnitude as the $IC_{50}$ values obtained with the purified enzymatic isoform GSTP1-1.

To support this correspondence, the compound 6-(7-nitro-2,1,3-benzoxadiazol-4-ylamino)ethanol was tested on the various cell lines and it was seen to have no inhibition activity with regard to the enzymatic isoform GSTP1-1, but showed an $IC_{50}$ of about 2 μM for the enzymatic isoform GSTM2-2. This compound manages to easily penetrate the cells, as may bededuced by the intense fluorescence recorded after 6 hours of incubation with various concentrations of 6-(7-nitro-2,1, 3-benzoxadiazole-4-ilamino)hexanol. All the tested cancer cell lines were still viable after 48 hours of incubation with 50 μM 6-(7-nitro-2,1,3-benzoxadiazol-4-ylamino)hexanol.

Table 3 reports the values of specific activity for GST (protein unit/mg) calculated in the cell lines used in the cytotoxicity trial.

TABLE 3

Specific activity of GST (protein unit/mg)

| | Cell lines | | | |
|---|---|---|---|---|
| | CEM1.3 | GLC-4 | K562 | HepG2 |
| Specific activity | 0.21 | 0.35 | 0.52 | 0.02 |

The cancer cell line that showed more resistance to treatment with the 7-nitro-2,1,3-benzoxadiazole derivatives is the one of the hepatic carcinoma HepG2. This cancer cell line also presents the lowest GST specific activity, as may be seen in Table 3, as well as a GST isoenzymatic make-up that is different from that of the other cancer cell lines.

Indeed, characterisation studies carried out on a large number of cell lines confirm that GSTP1-1 is the dominant enzymatic isoform in most cancer cell lines (1-30 μg/mg protein) and that the high levels of expression of this isoenzyme seem to be correlated to the proliferative capacity and to the immortalisation of these cancer cell lines (*Mol. Pharmacol.* 50, 1996, 149-159).

Instead, in the HepG2 cancer cell line, GSTP1-1 concentration is very low and the dominant enzymatic isoform is GSTA1-1, whose concentration in absolute terms is still about 1% of the concentration of GSTP1-1 found in most cancer cell lines (*Biochim Biophys Acta* 1225, 1994, 223-230).

Finally, it is interesting to note how the highest cytotoxicity of the tested anticancer compounds was found for the CEM 1.3 and K562 leukaemia cell lines, which are evidently more sensitive to this type of intervention with respect to solid cancer lines.

The Capacity of 7-nitro-2,1,3-benzoxadiazole Derivatives to Increase the Cytotoxicity of Anticancer Drugs on Resistant Cells In cancer cells the resistance to many anticancer drugs is often associated with a high expression of P-glycoprotein, a membrane protein belonging to the overall family of ABC transporters (ATP-binding cassette). This experiment envisaged testing the effect of 6-(7-nitro-2,1,3-benzoxadiazol-4-ylthio)hexanol on the toxicity of the vinblastine drug for CEMVBL100, a leukaemia line resistant to vinblastine (hyperexpressing P-glycoprotein).

Experimental Procedure—

The cells were placed in 96-well strips at a density of 15,000 cells per well, in a volume of culture medium of 100 μl. After 24 hours, a suitable concentration of between 25 nM and 1000 nM of vinblastine was added to the culture medium. The test was carried out both in the absence and in the presence of various concentrations of 6-(7-nitro-2,1,3-benzoxadiazol-4-ylthio)hexanol ranging between 0.1 μM and 1 μM. At the same time, some control trials were arranged by adding to the wells the solvent in which the compound was dissolved (% v/v of DMSO in PBS). All measurements were carried out in quadruplicate. After 48 hours of incubation, a dosage-response profile was obtained by using the SRB test (*J. Natl. Cancer. Inst.* 82, (1990), 1107-1112, loc. cit.). The toxicity of 6-(7-nitro-2,1,3-benzoxadiazol-4-ylthio)hexanol alone was also assessed for the resistant leukaemia line CEMVBL100.

Results—

As Table 4 shows, 6-(7-nitro-2,1,3-benzoxadiazol-4-ylthio)hexanol (0.5 µM) causes a marked increase in the sensitivity of leukaemia cells to the vinblastine drug.

TABLE 4

Effect of 6-(7-nitro-2,1,3-benzoxadiazol-4-ylthio)hexanol on the cytotoxicity of vinblastine ($IC_{50}$ nM)

| | 7-nitro-2,1,3-benzoxadiazole derivative | |
|---|---|---|
| | absent | 0.5 µM |
| CEM VBL100 | 340 | 50 |

It should also be noted that the CEMVBL100 cell line does not show a marked increase in resistance, in terms of $IC_{50}$, with respect to other cell lines which do not highly express P-glycoprotein. This finding suggests that the hyperexpression of P-glycoprotein does not interfere with the cytotoxic action of derivatives of 7-nitro-2,1,3-benzoxadiazole.

Analysis of Apoptosis in K562 and CEM1.3 Cell Lines

Induction of apoptosis in cells by the 7-nitro-benzofurazan derivative No. 2 was determined by measuring caspase-3 activation and by both morphological and flow-cytometric analysis.

Caspase-3 Activation

Experimental Procedure—

Caspase-3 activation plays a critical role in initiating the active phase of apoptosis that results in cell death. Thus, caspase-3 protease activity can be used to monitor apoptosis.

Pellets of cells at different times of incubation with 7-nitro-benzofurazan derivative No. 2 (10 µM and 2 µM with K562 and CEM1.3 respectively), were resuspended with lysis buffer (100 mM Hepes, pH 7.6, 0.1% Chaps, 1 mM EDTA, 1 mM Phenyl-methyl-sulphonyl-fluoride and 10 mM DTT) for 20 min on ice and cells were disrupted by 10-s sonication. Lysates, after centrifugation, were utilized to measure the caspase-3 activity. The substrate utilized was the model fluorescent peptide Ac-DEVD-AFC (Acetyl-Asp-GluVal-Asp-7-amino-4-trifluoromethyl coumarin) which was proteolyzed by caspase-3 resulting in a fluorescence emission at 505 nm (excitation at 400 nm). As control, lysates were incubated 30 min at 30° C. with the caspase inhibitor DEVD-CHO before evaluation of enzyme activity. Caspase activity was expressed as fluorescence change observed per minute per number of cells.

Results—

Incubation with 7-nitro-benzofurazan derivative No. 2 triggers activation of caspase-3 in both CEM1.3 and K562 cell lines. As shown in FIG. 3, a strong increase of caspase-3 in K562 was observed after 24 h of derivative No. 2 treatment. A similar result was obtained with CEM1.3 cells.

Morphological Analysis

Experimental Procedure—

K562 and CEM1.3 cell lines were treated for 24 h with 10 µM and 2 µM derivative No. 2 respectively. Apoptotic cells were detected with the fluorescence microscope by analyzing the nuclear fragmentation after staining with Hoechst 33342 (Calbiochem-Novabiochem) dye.

Results—

Representative data with K562 cells show chromatin condensation and nuclear fragmentation, which represent the final steps of apoptosis.

Flow Cytometric Analysis

Experimental Procedure—

Cells were washed in PBS, and stained with propidium iodide and with the impermeant dye Annexin V-FITC (Bender MedSystems, Vienna, Austria). The stained cells were analysed using a FACScan Flow Cytometer (Becton-Dickinson, CA). Data were recorded and statistically analysed by WinMDI version 2.8 software. Simultaneous staining of cells with Annexin V-FITC and PI allows the discrimination of intact cells, early apoptotic and late apoptotic or necrotic cells.

Results—

FIG. 4 shows the results of flow cytometric analysis performed on both K562 and CEM1.3 cell lines. A progressive increase of apoptotic cells was observed up to 24 h incubation time. 12 h treatment with derivative No. 2 induces 30% and 34% of apoptosis in K562 and CEM1.3 cell lines respectively while, after 24 h, the apoptosis raises to 41% and 47% in K562 and CEM1.3 cell lines respectively.

In conclusion, the results obtained with three different experimental approaches clearly show the pro-apoptotic ability of the 7-nitro-benzofurazan derivative in the CEM and K562 leukaemia cell lines.

Definition of the Intracellular Mechanism

The mechanism by which the GST inhibitor induces apoptosis is partly delineated below, where the interaction of derivative No. with the intracellular JNK-mediated pathway in lymphoblastoid CEM and in myelogenous K562 leukaemia cell lines is described.

Western Blot Analysis and Immunoprecipitation Experiment

Experimental Procedure—

Cells were washed with PBS and collected by centrifugation. The cell pellets were resuspended in lysis buffer containing 10 mM Tris-HCl (pH 7.4), 5 mM EDTA, 150 mM NaCl, 0.5% IGEPAL CA-630, and protease inhibitors (Sigma Co.). After 30-min incubation on ice, cells were disrupted by 10 s sonication. Lysates were then centrifuged and supernatants were loaded on 12% polyacrylamide gel and transferred onto a nitrocellulose membrane. Polyclonal anti-GSTP1-1 (1:1000); anti-c-Jun and anti-JNK (1:200) or monoclonal anti-phospho-activated c-Jun and JNK isoforms (1:200; Santa Cruz Biotechnology, Santa Cruz, Calif.); and β-actin (1:5000; Sigma Co.) were used as primary antibodies. β-actin was used as loading control.

For the immunoprecipitation analysis, cell pellets were resuspended in lysis buffer, and cells were disrupted by 10-s sonication. Lysates were then centrifuged at 14,000 g for 15 min at 4° C. Proteins were incubated in lysis buffer with anti-JNK antibody for 2 h at 4° C. Immunocomplexes were absorbed with protein A-Sepharose for 30 min at 4° C. After three washes with lysis buffer, immune pellets were boiled in SDS sample buffer. Proteins were loaded on 15% SDS-polyacrylamide gel and transferred to nitrocellulose. GST, JNK and phospho-JNK were detected by specific antibody.

Results—

FIGS. 5 (A, B and C) shows Western blot analyses of K562 and CEM1.3 cell lines treated with 10 µM and 2 µM derivative No. 2 respectively.

The Western blot analysis shows the basal and phosphorylated forms of both JNK and c-Jun. In both cell lines phospho-JNK is clearly increased after half an hour incubation with derivative No. 2 and it remains at high levels up to 24 h.

Phosphoactivation trend of c-Jun in K562 cell line is similar to the activation of JNK; it is rapidly detected after half an hour incubation with derivative No. 2 and it remains at high levels up to 12 hours (Panel A). Phosphoactivation of c-Jun in CEM1.3 cell line follows a different trend; a rapid increase of phospho-c-Jun is observed after half an hour on derivative No. 2 addition but it decreases rapidly and reaches the basal level after 12 h of treatment (Panel C).

These data suggest that apoptosis induction is dependent on the activation of JNK/c-Jun pathway even if the modality of cell response appears to be different. In particular, a hysto-type-dependent induction of mitogenactivated protein (MAP) kinase pathway could be hypothesized.

To assess if cell treatment with derivative No. 2 affects the amount of GST-JNK complex, K562 cell lysates were immunoprecipitated with an anti-JNK antybody and used for Western blot analysis. FIG. 5, Panel B, shows that the amount of GSTP1-1 that co-precipitates with JNK is rapidly decreased in the derivative No. 2-treated cells and slightly increases only after 3 h.

Thus, the activation of JNK/c-Jun pathway occurs via dissociation of GSTP1-1 from the GST-JNK complex triggered by derivative No. 2.

The foregoing allows the following conclusion to be drawn. In response to a multitude of stimuli that induce oxidative stress, including UV irradiation and anticancer drugs, the activation of MAP kinase family is necessary for the activation of genes and post-translational modification of proteins necessary for the induction of apoptosis. Beside the redox activation of this signalling pathway, addition of the GSH peptidomimetic compound (TER117) and its diethyl ester (TER199), a specific inhibitor of the GSTP1-1 isoenzyme, causes a dissociation of the GSTP1-1-JNK complex resulting in a JNK activation. Activation of JNK induces phosphorilation of the substrate c-Jun that regulates the transcription of genes involved in cell apoptosis. (*J. Pharmacol. Exp. Ther.* 296, (2001) 1-6).

Likewise, the 7-nitro-benzofurazan derivatives of in the present invention are very efficient GST inhibitors that could prime the cell for apoptosis by inducing the dissociation of the GSTP1-1 from JNK. It has been shown that the 7-nitro-benzofurazan derivative No. 2 behaves like a suicide substrate for GSTs: it is conjugated with GSH in the GST active site, leading to a σ-adduct intermediate which strongly inhibits the enzyme ($K_D=4\times10^{-8}$ M with GSTP1-1). This peculiar interaction suggests that GSTP1-1 is a very select target for this molecule. Inside the cell, the 7-nitro-benzofurazan derivative N° 2 induces the dissociation of the GSTP1-1 from JNK that results in the phosphoactivation of both JNK and c-Jun. The 7-nitro-benzofurazan derivative No. 2 triggers a typical process of apoptosis in K562 and CEM1.3 cells that includes cell shrinkage, phospholipid phosphatidyl-serine translocation to the cell surface, caspase activation and chromatin condensation.

Test of Acute Toxicity In Vivo

The test used 25 females of the BDF1 mouse strain (18-20 g Clarles River Lab. Lecco, Italia) divided into 5 groups of 5 mice each. Three groups were treated with a single administration, through intraperitoneal injection (i.p.), with 6-(7-nitro-2,1,3-benzoxadiazol-4-ylthio)hexanol at the following concentrations: a) 125 mg/kg, b) 25 mg/kg, c) 5 mg/kg. The remaining two groups were used as controls and envisaged the following administrations: d) an olive oil vehicle containing 2.5% DMSO, and e) a physiological solution.

The mice were followed up for 15 days, providing them with abundant food and water and recording the weight variations of each mouse. The recorded weight trend is reported in the diagram attached as FIG. 6, which shows that, even after 15 days of treatment, the mice presented only slight weight variations. Moreover, the weight of each mouse's liver and spleen was checked to see whether it remained within the norm, thus suggesting the absence of toxicity of 6-(7-nitro-2,1,3-benzoxadiazol-4-ylthio)hexanol even at the maximum concentration used (125 mg/kg).

All the data obtained contribute to confirming that the considerable cytotoxic activity of the derivatives of 7-nitro-2,1,3-benzoxadiazole on cancer cells is due to the inhibition of the detoxifying and anti-apoptotic activity of GSTP1-1 and that cancer cells are the primary target of these compounds since they hyperexpress GSTP1-1.

The 7-nitro-2,1,3-benzoxadiazole derivatives according to the present invention thus find a promising possible use as anticancer agents. Moreover, they can be used in combination with other chemotherapeutic agents to prevent, reduce or eliminate the drug-resistance effect shown in patients undergoing anticancer chemotherapy.

The present invention has been disclosed with particular reference to some specific embodiments thereof, but it should be understood that modifications and changes may be made by the persons skilled in the art without departing from the scope of the invention as defined in the appended claims.

The invention claimed is:

1. A method of inhibiting glutathione S-transferase (GST) enzyme in the treatment of cancer, which method comprises: administering to a patient in need thereof an effective amount of a derivative of 7-nitro-2,1,3-benzoxadiazole of the formula:

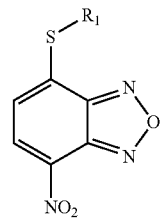

wherein $R_1$ is a linear, branched or cyclic alkyl with up to 12 carbon atoms, one hydrogen atom of $R_1$ being optionally substituted with one group selected from the group consisting of $OR_2$, $NO_2$, and $NR_2R_3$, wherein $R_2$ and $R_3$ are each independently selected from the group consisting of H, linear, branched or cyclic alkyl and alkenyl or alkynyl with up to 12 carbon atoms, and wherein said S—$R_1$ group is not a good leaving group.

2. The method according to claim 1, wherein $R_1$ is a linear or branched hydroxyalkyl with up to 12 carbon atoms.

3. The method according to claim 2, wherein $R_1$ is chosen from 4-hydroxybutyl and 6-hydroxyhexyl.

4. The method according to claim 3, wherein the 7-nitro-2,1,3-benzoxadiazole derivative corresponds to one of the following:

4-(7-nitro-2,1,3-benzoxadiazole-4-ylthio)butanol, and 6-(7-nitro-2,1,3-benzoxadiazole-4-ylthio)hexanol.

5. A method for treating a patient having cancer or at risk of developing cancer, said method comprising administering to said patient an effective amount of a compound of formula:

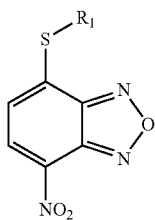

wherein $R_1$ is a linear, branched or cyclic alkyl with up to 12 carbon atoms, one hydrogen atom of $R_1$ being optionally substituted with one group selected from the group consisting of $OR_2$, $NO_2$, and $NR_2R_3$, wherein $R_2$ and $R_3$ are each independently selected from the group consisting of H, linear, branched or cyclic alkyl and alkenyl or alkynyl with up to 12 carbon atoms, and wherein said S—$R_1$ group is not a good leaving group.

6. The method according to claim 5, wherein said patient has human myeloid leukemia.

7. The method according to claim 5, wherein said patient has human hepatic carcinoma.

8. The method according to claim 5, wherein said patient has human T-lymphoblastic carcinoma.

9. The method according to claim 5, wherein said patient has human small cell lung carcinoma.

10. The method according to claim 5, wherein said patient has a cancer exhibiting hyperexpression of glutathione S-transferases (GST).

11. The method according to claim 1, wherein said S—$R_1$ group is an alkylthio group.

12. The method according to claim 5, wherein said S—$R_1$ group is an alkylthio group.

13. The method of claim 1, wherein said cancer is selected from the group consisting of:
human myeloid leukaemia, human T-lymphoblastic leukaemia, human hepatic carcinoma and human small cell lung carcinoma.

14. The method of claim 5, wherein said cancer is selected from the group consisting of: human myeloid leukaemia, human T-lymphoblastic leukaemia, human hepatic carcinoma and human small cell lung carcinoma.

15. A method of inhibiting a glutathione S-transferase (GST) enzyme in an animal, the method comprising administering to the animal an effective amount of a derivative of 7-nitro-2,1,3-benzoxadiazole of the formula:

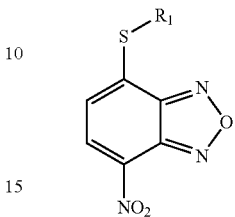

wherein $R_1$ is a linear, branched or cyclic alkyl with up to carbon atoms, one hydrogen atom of $R_1$ being optionally substituted with one group selected from the group consisting of $OR_2$, $NO_2$, and $NR_2R_3$, wherein $R_2$ and $R_3$ are each independently selected from the group consisting of H, linear, branched or cyclic alkyl and alkenyl or alkynyl with up to 12 carbon atoms, and wherein said S—$R_1$ group is not a good leaving group.

16. The method according to claim 15, wherein the GST enzyme is one of GSTP1-1, GSTA1-1, and GSTM2-2.

17. The method according to claim 15, wherein the animal is a human.

18. The method according to claim 15, wherein the derivative of 7-nitro-2,1,3-benzoxadiazole is
4-(7-nitro-2,1,3-benzoxadiazole-4-ylthio)butanol, or
6-(7-nitro-2,1,3-benzoxadiazole-4-ylthio)hexanol.

19. The method according to claim 15, wherein the GST enzyme is inside a cancer cell.

20. The method according to claim 15, further comprising administering to the animal one or more additional chemotherapeutic agents in combination with the derivative of 7-nitro-2,1,3-benzoxadiazole.

* * * * *